United States Patent
Di Nardo et al.

(10) Patent No.: US 9,868,783 B2
(45) Date of Patent: Jan. 16, 2018

(54) INHIBITION OF THE SYNTHESIS OF BETA-APP OR THE ACTIVITY OF THE A-β PEPTIDE IN THE CHOROID PLEXUS

(71) Applicants: CENTRE NATIONAL DE LA RECHERCHE SCIENTIFIQUE, Paris (FR); COLLEGE DE FRANCE, Paris (FR); INSTITUT NATIONAL DE LA SANTE ET DE LA RECHERCHE MEDICALE (INSERM), Paris (FR)

(72) Inventors: Ariel Di Nardo, Palaiseau (FR); Kenneth Lee Moya, Paris (FR); Karen Arnaud, Paris (FR); Alain Prochiantz, Paris (FR)

(73) Assignees: CENTRE NATIONAL DE LA RECHERCHE SCIENTIFIQUE, Paris (FR); COLLEGE DE FRANCE, Paris (FR); INSTITUT NATIONAL DE LA SANTE ET DE LA RECHERCHE MEDICALE, Paris (FR)

( * ) Notice: Subject to any disclaimer, the term of this patent is extended or adjusted under 35 U.S.C. 154(b) by 0 days.

(21) Appl. No.: 14/901,655

(22) PCT Filed: Jul. 4, 2014

(86) PCT No.: PCT/IB2014/062871
§ 371 (c)(1),
(2) Date: Dec. 28, 2015

(87) PCT Pub. No.: WO2015/001532
PCT Pub. Date: Jan. 8, 2015

(65) Prior Publication Data
US 2016/0159889 A1  Jun. 9, 2016

(30) Foreign Application Priority Data
Jul. 4, 2013  (FR) ..................... 13 56551

(51) Int. Cl.
| | | |
|---|---|---|
| *C12N 15/11* | (2006.01) | |
| *C12N 15/63* | (2006.01) | |
| *C12N 15/861* | (2006.01) | |
| *C12N 15/86* | (2006.01) | |
| *C12N 15/00* | (2006.01) | |
| *A61K 48/00* | (2006.01) | |
| *C07K 16/18* | (2006.01) | |
| *A61K 39/00* | (2006.01) | |
| *C12N 15/113* | (2010.01) | |

(52) U.S. Cl.
CPC ......... *C07K 16/18* (2013.01); *A61K 39/0007* (2013.01); *C12N 15/113* (2013.01); *A61K 48/00* (2013.01); *A61K 2039/54* (2013.01); *C07K 2317/622* (2013.01); *C07K 2317/76* (2013.01); *C12N 2310/14* (2013.01); *C12N 2750/14143* (2013.01)

(58) Field of Classification Search
CPC .............. A61K 38/00; A61K 2039/505; A61K 2300/00; A61K 48/00; A01K 2217/05; C07K 14/4711; C07K 14/47; C07K 2317/565; C07K 2317/622; C12N 2310/14; C12N 2310/11; C12N 15/86; G01N 33/6896; G01N 2800/2821
See application file for complete search history.

(56) References Cited

U.S. PATENT DOCUMENTS

2008/0038227 A1* 2/2008 Torres Aleman .. A01K 67/0276
424/93.2
2011/0081717 A1  4/2011 Inoue et al.

FOREIGN PATENT DOCUMENTS

| WO | WO2006053787 | * | 5/2006 | ............. C12N 15/85 |
| WO | 2006/118959 A2 | | 11/2006 | |
| WO | 2009/122401 A2 | | 10/2009 | |

OTHER PUBLICATIONS

Tayebati. Mech. Ageing Dev. 2006. 127: 100-8.*
Burgess et al. J of Cell Bio. 1990, 111:2129-2138.*
't Hart et al. Curr. Opin. Neurol. 2003. 16: 375-383.*
Anger. Neurotoxicology 1991. 12: 403-13.*
Pawson et al. 2003, Science 300:445-452.*
Bowie et al. Science, 1990, 247:1306-1310.*
Doge et al. Mol. Ther. 2008; 16:1056-1064.*
Cachon-Gonzalez et al. Mol. Ther. 2012; 20:1489-1500.*
Donsante et al. Mol. Ther. 2011, online publication Aug. 30, 2011.*
Regev et al. PNAS, 2010; 107:4424-4429.*
Fukuchi, K., et al., "Anti-Aβ Single-Chain Antibody Delivery Via Adeno-Associated Virus for Treatment of Alzheimer's Disease," Neurobiology of Disease 23(3):502-511, Sep. 2006.
Piao, W., et al. "Efficient in Vivo Delivery of Antisense Oligonucleotide to Choroid Plexus," Journal of Medical and Dental Sciences 60(1):9-16, Mar. 2013.
Shimizu, S., "Routes of Administration," In: "The Laboratory Mouse," 527-541, Jan. 2004.
Vite, C.H., et al., "Adeno-Associated Virus Vector-Mediated Transduction in the Cat Brain," Gene Therapy 10:1874-1881, Jan. 2003.
Zhou, Z., et al., "The Roles of Amyloid Precursor Protein (APP) in Neurogenesis, Implications to Pathogenesis and Therapy of Alzheimer Disease (AD)," 5(4): 280-292, Jul. 2011.
International Search Report dated Jan. 12, 2014, issued in corresponding International Application No. PCT/IB2014/062871, filed Jul. 4, 2014, 4 pages.
Written Opinion of the International Searching Authority, issued in corresponding International Application No. PCT/IB2014/062871, filed Jul. 4, 2014, 5 pages.

(Continued)

*Primary Examiner* — Chang-Yu Wang
(74) *Attorney, Agent, or Firm* — Christensen O'Connor Johnson Kindness PLLC

(57) ABSTRACT

The invention relates to the treatment of neurodegenerative diseases, in particular Alzheimer's disease, by inhibition of the synthesis of βAPP or of the activity of the Aβ peptide in the choroid plexus.

9 Claims, 6 Drawing Sheets

(56) References Cited

OTHER PUBLICATIONS

Baird, A., et al., "Targeting the Choroid Plexus-CSF-Brain Nexus Using Peptides Identified by Phage Display," Methods in Molecular Biology 686:483-498, Jan. 2011 (Author Manuscript provided, PMCID:PMC4224277, available in PMC Nov. 7, 2014, 16 pages).
Bolos, M., et al., "Neurogenic Effects of β-Amyloid in the Choroid Plexus Epithelial Cells in Alzheimer's Disease," Cellular and Molecular Life Sciences 70(15):2787-2797, Aug. 2013.
Crossgrove, J.S., et al., "The Choroid Plexus Removes β-Amyloid From Brain Cerebrospinal Fluid," Experimental Biology and Medicine (Maywood) 230(10):771-776, Nov. 2005 2011 (Author Manuscript provided, PMCID:PMC3982214, available in PMC Apr. 10, 2014, 13 pages).
Gonzalez, A.M., et al., "Epidermal Growth Factor Targeting of Bacteriophage to the Choroid Plexus for Gene Delivery to the Central Nervous System via Cerebrospinal Fluid," Brain Research 1359:1-13, Nov. 2010 2011 (Author Manuscript provided, PMCID:PMC2955767, available in PMC Nov. 4, 2011, 20 pages).
Van Uden, E., et al., "Increased Extracellular Amyloid Deposition and Neurodegeneration in Human Amyloid Precursor Protein Transgenic Mice Deficient in Receptor-Associated Protein," Journal of Neuroscience 22(21):9298-9304, Nov. 2002.
Written Opinion of the International Searching Authority dated Dec. 1, 2014, issued in corresponding International Application No. PCT/IB2014/062871, filed Jul. 4, 2014, 5 pages.
International Preliminary Report on Patentability dated Jan. 5, 2016, issued in corresponding International Application No. PCT/IB2014/062871, filed Jul. 4, 2014, 1 page.

\* cited by examiner

A

B

C

A

B

INHIBITION OF THE SYNTHESIS OF BETA-APP OR THE ACTIVITY OF THE A-β PEPTIDE IN THE CHOROID PLEXUS

CROSS-REFERENCE TO RELATED APPLICATION

This application is the National Stage of International Application No. PCT/IB2014/062871, filed on Jul. 4, 2014, the entirety of which is incorporated herein by reference.

STATEMENT REGARDING SEQUENCE LISTING

The sequence listing associated with this application is provided in text format in lieu of a paper copy and is hereby incorporated by reference into the specification. The name of the text file containing the sequence listing is 55118_ST25.txt. The text file is 6 KB; was created on Aug. 25, 2017; and is submitted via EFS-Web.

The invention relates to means for restoring the physiological function of the precursor of the amyloid protein (βAPP) and for reducing the production of β-amyloid peptide, which may be used within the scope of prevention or treatment of neurodegenerative diseases, notably Alzheimer's disease.

The β-amyloid peptide (Aβ peptide) is the major constituent of extracellular amyloid deposits observed in the brain cortex of patients affected with Alzheimer's disease. This peptide stems from the cleavage of the transmembrane protein βAPP (for <<β-amyloid precursor protein>>). It is important to recall that the only source of peptide AR is the β-APP protein and that a reduction of the βAPP protein causes ipso facto a reduction in the production of the Aβ peptide. It must also be recalled that the βAPP protein has physiological functions and that one of them is to regulate adult neurogenesis (CAILLE et al., Development, 131, 2173-81, 2004).

The Aβ peptide results from the maturation of the βAPP protein via the so called <<amyloidogenic>> route, involving the successive action of two protease activities, β-secretase and γ-secretase, which respectively release the N- and C-terminal ends of the peptide.

The accumulation of Aβ peptides in the extracellular medium induces alterations of the cell membranes causing massive entry of calcium into the cell and being accompanied by an inflammatory reaction. These lesions would cause neuronal death.

An alternative proteolytic maturation route of the βAPP protein is the so called <<non-amyloidogenic>> route; in this route, another enzyme, α-secretase, cuts the βAPP at the middle of the Aβ sequence. This cleavage prevents the formation of the Aβ peptide and releases a soluble and secreted form called sAPP, which has neuroprotective properties and a mitogenic function on adult neural cell strains (CAILLE et al., Development, 131, 2173-81, 2004). The production of the sAPP is therefore incompatible with that of the βA4 generated by the action of the beta-secretase (N-terminal) and the gamma-secretase (C-terminal).

The protein βAPP is expressed in many tissues of the organism, and notably by the neurones, including at the brain level.

The choroid plexus are structures localized at the ventricles, more particularly at the roof of the fourth ventricle and of the junction between the lateral ventricles of the brain and the third ventricle. They consist of an epithelium consisting of ependymal cells associated by narrowed junctions and resting on a basal membrane which separates them from a connective and vascular tissue stroma consisting of a network of fenestrated blood capillaries, and of collagen fibers produced by the fibroblasts present in the stroma.

The choroid plexuses produce the cerebrospinal liquid (CSL), by playing a role of a selective barrier allowing the passage of certain molecules between the blood and the CSL, and by blocking others. They also synthesize a certain number of proteins, which are secreted in the CSL. Although the presence of βAPP in choroid plexuses has been reported (SASAKI et al., Brain Res, 755, 193-201, 1997), its expression level had never been determined before.

The inventors have now ascertained, during an analysis by sequencing of the RNAs of the epithelial cells of the choroid plexus, that the gene coding for βAPP was part of those which were the most strongly expressed in this structure, and that the expression level of this protein in the choroid plexus was much greater than the one observed in other regions of the brain known previously for expressing it at a high level. They also observed a very high expression of the protein APLP-2, which belongs to the same family as βAPP and which like the latter may generate by proteolytic maturation a soluble form (sAPLP-2) having neuroprotective and neurotrophic properties, but which, unlike βAPP does not form an Aβ peptide since APLP-2 does not contain the Aβ sequence (WASCO et al., Proc Natl Acad Sci USA, 89, 10758-62, 1992).

This observation made by the inventors of the quantitative importance of choroid plexuses as a source of βAPP gives the possibility of proposing that this brain structure be targeted for regulating therein the production of βAPP, either by increasing it, or by decreasing it. It is clear that decreasing the expression of βAPP in choroid plexuses should decrease that of the peptide Aβ. This structure may also be targeted for strategies aiming at blocking or reducing the activity of the Aβ peptide.

The present invention relates to the targeting of the choroid plexus in strategies for regulating the synthesis of the βAPP protein or of addressing an inhibitor of the activity of the Aβ peptide, within the scope of the treatment of a neurodegenerative disease.

The object of the present invention is accordingly an inhibitor of the synthesis of the βAPP protein or of the activity of the Aβ peptide or an expression vector coding for said inhibitor, for its use in the treatment of a neurodegenerative disease, by targeting said inhibitor in choroid plexuses in order to decrease therein the production or the activity of said Aβ peptide.

If one chooses to inhibit the synthesis of the βAPP protein, the inhibitor used may be advantageously selected from antisense oligonucleotides and interfering RNAs directed against the gene coding for this protein.

The functionalities of the βAPP protein related to the production of sAPP may be compensated by the protein APLP-2, which is also strongly expressed in choroid plexuses.

If this compensation is not sufficient, it is possible to overexpress sAPP in a recombinant form in epithelial cells of choroid plexuses. In this case, the antisense oligonucleotide or the iRNA used for inhibiting the synthesis of the βAPP protein will be preferentially directed against a region of the gene coding for the C-terminal portion of this protein, in order not to interfere with the synthesis of recombinant sAPP.

If one chooses to inhibit the activity of the Aβ peptide, it is possible to use for this purpose an antibody or an antibody fragment selectively directed against this peptide and capable of blocking its activity. Many antibodies having this property are known per se; as non-limiting examples, mention will be made of scFVAβ$^{1B}$, scFVAβ$_{KDE}^{1B}$ (SUDOL et al., Mol Ther, 17, 2031-40, 2009) scFV59 (FUKUCHI et al., Neurobiol Dis, 23, 502-11, 2006), or CBAβ342 (ZHANG et al., Neurobiol Dis, 14, 365-79, 2003).

Vectors which may used within the scope of present invention for expressing antisense oligonucleotides, iRNAs, sAPP, or antibodies directed against the peptide Aβ, in the cells of the choroid plexus are viral vectors preferentially targeting these cells. For example these are vectors derived from adeno-associated viruses (AAV) of serotypes 2, 4 or 5 (CACHON-GONZALEZ et al., Mol Ther, 20, 1489-500, 2012; DODGE et al., Mol Ther, 18, 2075-84, 2010; DONSANTE et al., Mol Ther, 19, 2114-23, 2011; WATSON et al., Hum Gene Ther, 16, 49-56, 2005).

Regardless of the selected vector, it is also possible to place the antisense oligonucleotide; the iRNA, the sAPP or the antibody directed against the peptide Aβ, will be placed in the selected vector, under control of a specific promoter of the cells of the choroid plexus; as non-limiting examples of promoters which may be used within this scope, mention will be made of the promoter of the gene CRFR2β (REGEV et al., Proc Natl Acad Sci USA, 107, 4424-9, 2010), the promoter of transthyretin (COSTA et al., Molecular and Cellular Biology, 6, 4697-708, 1986), or that of the gene GPR125 (PICKERING et al., BMC Neuroscience, 9, 97, 2008).

The choroid plexus also has the advantage of being easily accessible by not very invasive routes, in particular via the injection of pharmacological substances into the venous system and, more favorably, in the retro-orbital sinus which is quite near the basolateral face of the choroid plexus. It is therefore possible to address to the choroid plexus, molecules or viral vectors which may transiently or permanently modify the expression and/or the secretion of βAPP, of βA4 and of sAPP by the choroid plexus.

The object of the present invention is also a method for treating a neurodegenerative disease, comprising the targeting in the choroid plexuses of a patient, of an effective amount of an inhibitor of the synthesis of the βAPP protein or of the activity of the Aβ peptide or of an expression vector coding for said inhibitor, in order to decrease the production or the activity of said Aβ peptide in the choroid plexuses of said patient.

Said method may also comprise the targeting in the choroid plexuses of said patient, of an effective amount of a functional soluble form of the βAPP protein, for restoring or increasing therein a physiological function of said βAPP protein, notably neurogenesis. The functional soluble form of the βAPP protein is a soluble protein derived from the βAPP protein which retains the physiological functions of the βAPP protein; this is notably sAPP. According to the method of the invention, said inhibitor and said soluble form of the βAPP protein are administered simultaneously, separately or sequentially.

The object of the present invention is also a combined preparation, comprising:
(i) an inhibitor of the synthesis of the βAPP protein or of the activity of the Aβ peptide or an expression vector coding for said inhibitor and
(ii) a functional soluble form of the βAPP protein or an expression vector coding for said soluble form,
for simultaneous, separate or sequential use in the treatment of a neurodegenerative disease, by targeting the choroid plexuses of the patient in order to decrease therein the production or the activity of said Aβ peptide and restore or increase a physiological function of said βAPP protein, notably neurogenesis.

Neurodegenerative diseases which may be treated according to the invention are notably the sporadic and family forms of Alzheimer's disease.

The present invention will be better understood by means of the additional description which follows, which refers to non-limiting examples demonstrating the expression of βAPP in choroid plexuses and describing the construction of viral vectors giving the possibility of regulating this expression or inhibiting the activity of the βA4 peptide, as well as to the appended drawings wherein:

FIG. 1 illustrates the relative levels of the mRNAs of the genes App, Aplp1 and Aplp2 added to those of the housekeeping gene HPRT, in the $4^{th}$ ventricle (ChP 4V), the lateral ventricles (ChP LV), the hippocampus (Hc), the subventricular area (SVZ) and the primary visual cortex (V1) of mice about eight weeks old.

FIG. 2 illustrates the detection of the transmembrane forms and secreted of the protein βAPP in the cerebrospinal liquid and the choroid plexus. A. Western Blot with an antibody directed against the N-terminal portion of the βAPP protein (extracellular APP domain), specific to the secreted form. B. Western Blot with an antibody directed against the C-terminal portion of the βAPP protein (C terminal APP), specific to the transmembrane form. CSFrat: cerebrospinal liquid of rats. CSFh: human cerebrospinal liquid. Mouse plexus: mouse choroid plexus.

FIG. 3 illustrates the specific targeting of the choroid plexuses by the AAV of serotype 5 (AAV5). The GFP activity of the brain of mice bearing the gene coding for GFP but only expressing it after recombination, was analyzed after injection into the cerebral ventricles, of an AAV5 either bearing or not the gene coding for the CRE recombinase. A. AAV5-CRE. B. control AAV5.

FIG. 4 illustrates the recombination of the βAPP gene in the choroid plexus. A. Schematic illustration of the non-recombinant βAPP gene (APPflox) and recombined by the CRE recombinase (APPΔ) in the APP$^{flox/flox}$ mouse line. APP$^{flox/flox}$ mice were injected with the protein CRE-Tat or a vehicle as a control into the cerebral ventricles. 15 days after the injection, the genomic DNA of the choroid plexus (plexus), of the hippocampus, of the brain cortex (cortex) and of the retina were analyzed by PCR (B) and the amount of protein fβAPP in the choroid plexus was quantified by a Western Blot (C).

EXAMPLE 1: EXPRESSION OF THE βAPP PROTEIN IN CHOROID PLEXUSES

We compared the expression level of βAPP and of two close molecules, APLP-1 and APLP-2, in the choroid plexus, the hippocampus, the subventricular zone and the primary visual cortex of a mouse of about eight weeks old.

After dissecting the tissues, the RNAs were extracted and the abundance of messenger RNAs for the genes APP, APLP1 and APLP2 determined by RT-qPCR by primers specific to each gene. The expression levels are reported relatively to that of a housekeeping gene, HPRT. The results are illustrated by FIG. 1 and Table 1 below.

Figure 1:
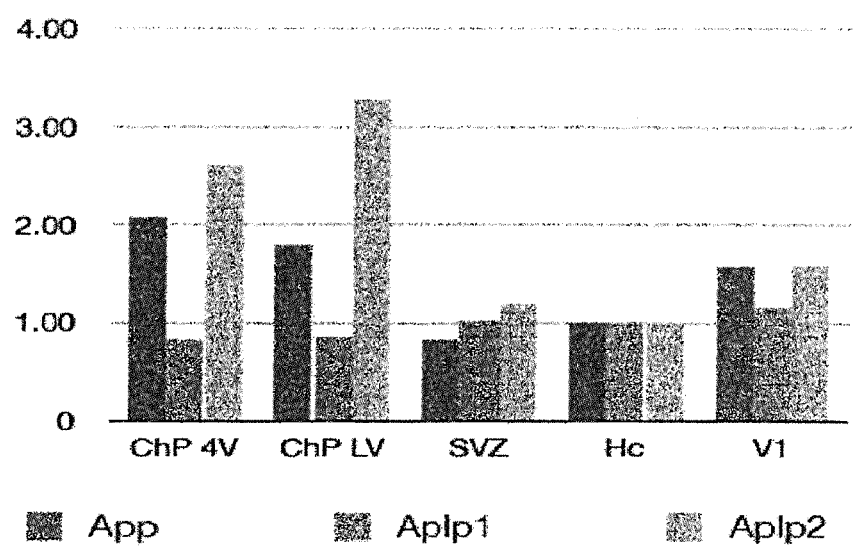

Caption of FIG. 1 and of Table 1: 4$^{th}$ ventricle: ChP 4V; lateral ventricles: ChP LV; hippocampus: Hc); subventricular zone: SVZ; primary visual cortex: V1.

TABLE 1

|  | App | Apip1 | Apip2 |
|---|---|---|---|
| ChP 4V | 2.07 | 0.82 | 2.61 |
| ChP LV | 1.80 | 0.86 | 3.28 |
| SVZ | 0.82 | 1.03 | 1.19 |
| Hc | 1.00 | 1.00 | 1.00 |
| V1 | 1.58 | 1.15 | 1.59 |

These results clearly show that the choroid plexus expresses twice to three times more APP and APLP2 transcripts than the other structures.

EXAMPLE 2: THE ENTIRE βAPP IS PRESENT IN THE CHOROID PLEXUS AND ITS SOLUBLE FORM IS SECRETED IN THE CSL

Figure 2:
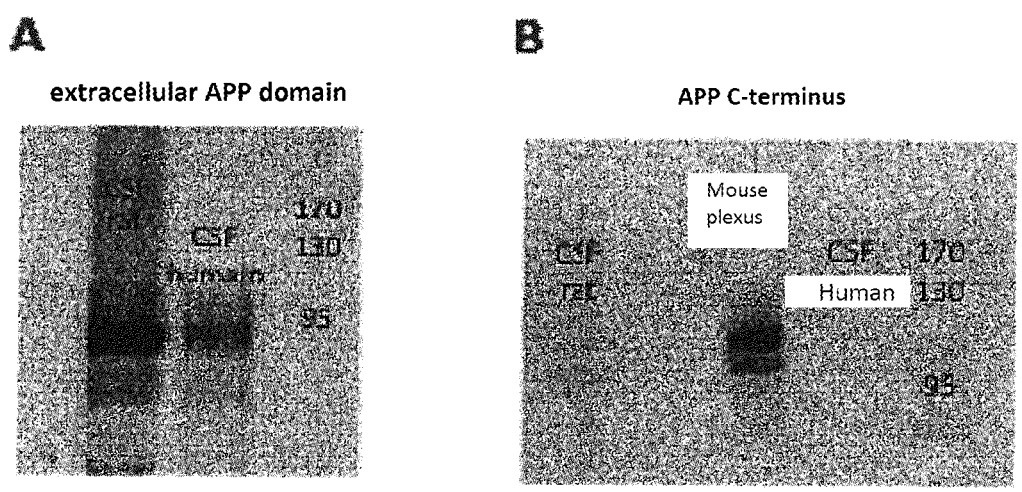

The choroid plexus of a rodent was analyzed by Western blot with an antibody directed against the C-terminal portion of βAPP (FIG. 2B). The antibody reveals a signal at 105 and 120 kDa corresponding to the entire and transmembrane form of βAPP. The presence of secreted βAPP (sAPP) in the cerebrospinal liquid (CSL) of the rodent and of humans was sought by Western blot with an antibody directed against the N-terminal portion of the protein (therefore extracellular and potentially secreted after cleavage by the alpha-secretase). The antibody reveals a signal around 90 kDa corresponding to the cleaved and secreted form of βAPP (sAPP) in the CSL (FIG. 2A).

EXAMPLE 3: THE AAV OF SEROTYPE 5 (AAV5) SPECIFICALLY TARGETS THE CHOROID PLEXUSES FOR GENETIC RECOMBINATION

Previously we showed that the fusion protein of the CRE recombinase with the peptide vector derived from the TAT protein of the HIV (CRE-TAT) injected into the cerebral ventricles of adult mice is capable of inducing a specific genomic recombination in the choroid plexus (SPATAZZA et al., Cell Reports 3: 1815-1823, 2013).

Figure 3:
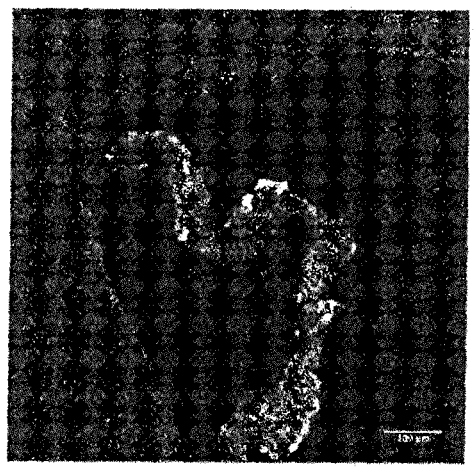
Figure 3:
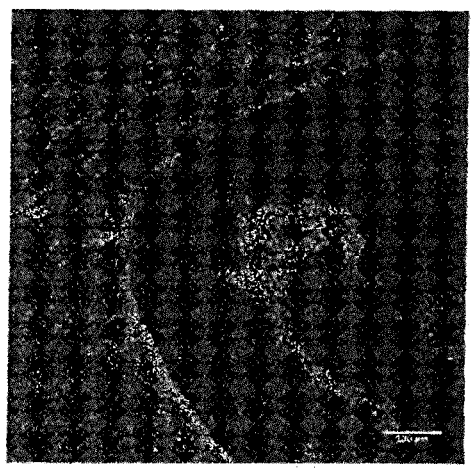

In order to demonstrate a viral vector specifically targets the choroid plexus, an AAV5 either bearing or not the gene coding for the CRE recombinase was injected into the cerebral ventricles of mice bearing the gene coding for GFP but only expressing it after recombination by CRE recombinase. FIG. 3A demonstrates that the virus has access to the choroid plexus but does not infect the neighboring parenchyma and that the CRE expressed by the viral genome induces expression of GFP in a large amount of cells of the choroid plexus.

EXAMPLE 4: THE GENE βAPP MAY BE RECOMBINED IN THE CHOROID PLEXUS

Figure 4:
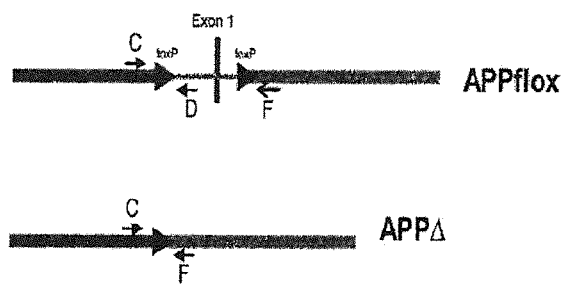
Figure 4:
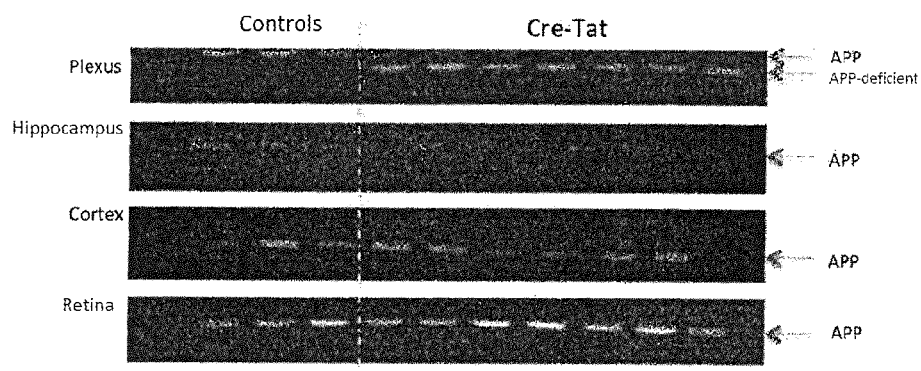
Figure 4:
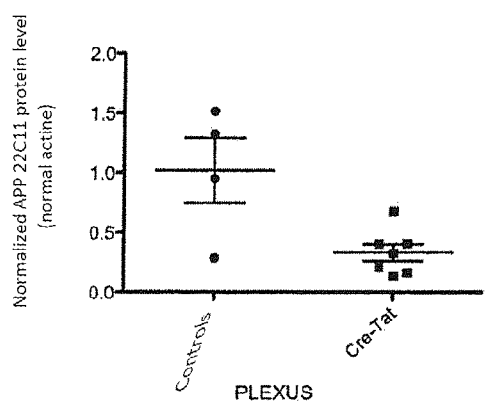

Adult APP$^{flox/flox}$ mice (MALLIM et al., Genesis 48: 200-206, 2010; FIG. 4A), were injected with the carrier or the CRE-TAT protein into the cerebral ventricles. Fifteen days later, the genomic DNA was extracted from different regions of the brain and analyzed by PCR. The gel of FIG. 4B demonstrates that the gene of the βAPP was specifically recombined in the choroid plexus, excluding other structures of the central nervous system like the retina, the neocortex or the hippocampus. Analysis by Western blot confirms that the amount of βAPP protein is significantly decreased in the choroid plexus 15 days after recombination (FIG. 4C).

EXAMPLE 5: DECREASE OF βAPP IN THE CHOROID PLEXUS CAUSES A REDUCTION IN THE NUMBER OF PROLIFERATIVE CELLS IN THE SUB-VENTRICULAR ZONE

Figure 5:
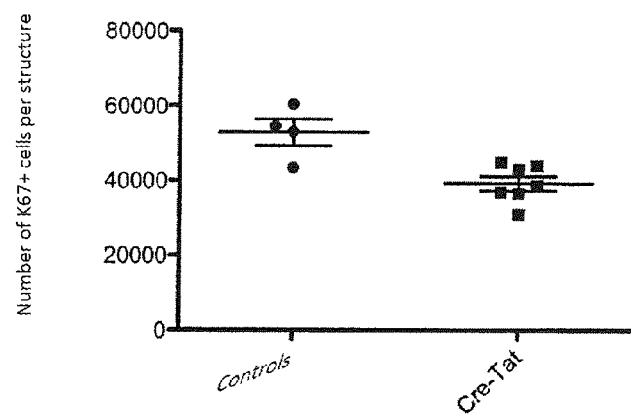
FIG. 5 illustrates the decrease in the number of proliferative cells (Ki67+) in the subventricular zone (SVZ), after decrease in the βAPP protein in the choroid plexus by genetic recombination of the βAPP gene.

The proliferative cells of mice in which the gene βAPP has been recombined (Example 4) were identified by means of an antibody directed against the protein Ki67 (proliferation marker) and then counted by stereology. Relatively to the control mice, the mice in which the gene βAPP was recombined have their neurogenesis (number of proliferative cells) decreased significantly (FIG. 5).

EXAMPLE 6: THE EXOGENUS SAPP INJECTED INTO THE CEREBRAL VENTRICLES INCREASES NEUROGENESIS IN SVZ

The recombinant sAPP was injected into the cerebral ventricles of adult wild mice of six weeks old. One and three weeks later, the proliferative cells are identified by means of the marker Ki67 as in Example 5. An increase in the number of proliferative cells is expected.

EXAMPLE 7: CONSTRUCTION OF A VIRAL VECTOR FOR EXPRESSING SAPP IN THE CHOROID PLEXUS

The sequence coding for sAPP (nt 201-2213 of NM_000484, Genbank, which is set forth in SEQ ID NO:3), is inserted into a lentiviral vector derived from pTRIPΔU3 [PGK+beta2/IRES2+eGFP+WPRE] (MASKOS et al., 2005, Nature 436: 103-107), downstream from the promoter FoxJ1 which is not active in neuronal cells (ZHANG et al., 2007, Am J Respir Cell Mol Biol 36: 515-519), and upstream from the sequence coding for an intermediate peptide (P2A, KIM et al, 2011, PloS one 6(4) e18556) followed by that of the GFP.

The resulting plasmid (pLFsAPP-P2Gfp) is co-transfected with plasmids coding for the viral proteins required in a suitable packing line (HEK 293T). The viral particles are then recovered in the culture medium, concentrated and titrated.

The obtained lentiviruses are injected into the retro-orbital sinus, from where they have preferred access to the choroid plexus.

EXAMPLE 8: CONSTRUCTION OF A VECTOR FOR EXPRESSING AN ANTIBODY WITH A SIMPLE CHAIN AGAINST Ba4

The mRNAs extracted from hybridomas expressing an anti-βA4 monoclonal antibody such as scFV Aβ$^{1B}$, scFVAβ$_{KDE}^{1B}$ (SUDOL et al., 2009, supra), scFV59 (FU-KUCHI et al., 2006, supra) or CBAβ342 (ZHANG et al., 2003, supra), are used for separately amplifying the variable portions of the heavy and lightweight chains according to the procedure described by BARBAS et al. (2001, "Phage display, a laboratory manual", CSHL Press) adapted in the laboratory (LESAFFRE et al., Neural Development, 2, 2, 2007). Position on either side of the coding sequence of a long flexible linker, these minigenes are fused with a label formed with 6 tag myc, and introduced into the bi-cistronic lentiviral vector described above (Cf. Example 7).

The resulting plasmid (pLFsabA4-P2Gfp) is used for producing lentiviruses which are injected as described above (cf. Example 7).

EXAMPLE 9: CONSTRUCTION OF A SMALL INTERFERING RNA FOR DECREASING THE EXPRESSION OF THE βAPP GENE AND THE AMOUNT OF βAPP PROTEIN

A small interfering RNA (iRNA or siRNA) was prepared; its sequence 5'-AUGAACUUCAUAUCCUGAGTC-3' (SEQ ID NO: 1) complementary of the sequence 5'-GACTCAGGATATGAAGTTCAT-3' (SEQ ID NO: 2) is specific to the DNA domain coding for a portion of the human Aβ peptide. Human cells of the HeLa line are cultivated and 24 h later a control siRNA (i.e., corresponding to no human sequence in the database BLAST) or the iRNA was transfected (100 pmol/100,000 cells). 48 hours later, the cells were lysed and the βAPP mRNA level analysed by RT-qPCR and the amount of βAPP protein by Western blot.

Figure 6:
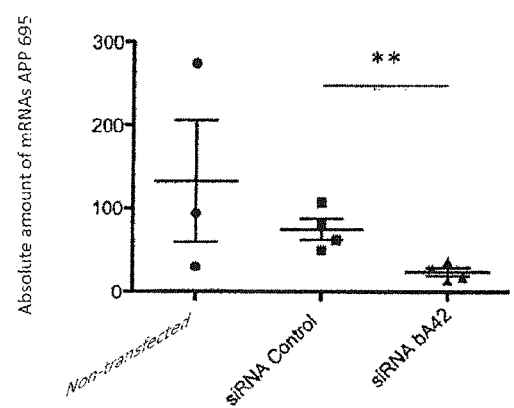
FIG. 6 illustrates the decrease of βAPP mRNA (A) and of fβAPP protein (B) in Hela cells transfected with an iRNA targeting the peptide Aβ.
Figure 6:
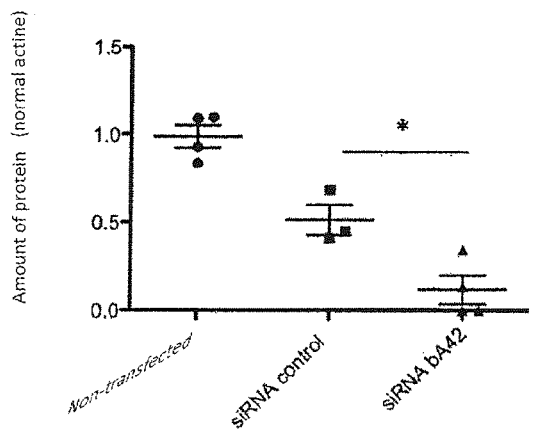

After transfection with RNAi, the βAPP mRNA level is significantly decreased (relatively to the cells transfected with the control siRNA), (FIG. 6A). The amount of βAPP protein is also decreased significantly in the cells transfected with iRNA (FIG. 6B).

EXAMPLE 10: USE AN AAV5 EXPRESSING A SMALL INTERFERING RNA FOR DECREASING THE EXPRESSION OF βAPP IN THE CHOROID PLEXUS AND DELAYING THE FORMATION OF SENILE PLATES IN THE BRAIN OF APP/PS1 MICE

An AAV5 expressing the shRNA corresponding to the small iRNA of Example 9 under the control of the promoter U6 was constructed. The mice bearing a "Swedish" mutation in the gene coding for βAPP and bearing a mutation in the gene coding for PS1 developed Aβ aggregates (senile plates) in the hippocampus and the neocortex from the age of 4 months. These mice are injected with AAV5-shRNA in the cerebral ventricles between 3 and 5 months and at 6 months, the size and the amount of the Aβ deposits are identified by marking with Thioflavin S and anti-Aβ antibodies are analysed. A decrease in the number of plates is expected.

The invention claimed is:

1. A method of decreasing the synthesis of βAPP in the choroid plexus of a patient affected with Alzheimer's disease, comprising administering an expression vector coding for an inhibitor of the βAPP protein to said patient targeting the choroid plexuses of said patient,
said inhibitor being selected from antisense oligonucleotides and interfering RNAs directed against the gene coding of said βAPP protein, and
said vector being derived from an adeno-associated virus allowing specific expression of said inhibitor in choroid plexus cells, and/or
said inhibitor being under control of a specific promoter of cells of the choroid plexus.

2. The method of claim 1, wherein said antisense oligonucleotide or interfering RNA is directed against a region of the mRNA coding for the C-terminal portion of the endogenous βAPP protein in order not to interfere with the synthesis of a soluble functional recombinant form of the βAPP protein encoded by nucleic acids 201-2213 of SEQ ID NO:3.

3. The method of claim 1, wherein said method reduces the Aβ peptide synthesis.

4. The method according to claim 1, wherein the vector is derived from an adeno-associated virus of serotype 2, 4, or 5.

5. The method according to claim 1, wherein said Alzheimer's disease is a sporadic or family form of Alzheimer's disease.

6. The method according to claim 1, wherein said vector is administered by injection into the retro-orbital sinus.

7. The method according to claim 1, wherein said vector is administered by injection into the venous system.

8. The method according to claim 1, wherein said vector is combined with a soluble functional recombinant form of the βAPP protein, wherein the antisense oligonucleotide or interfering RNA is directed against a region of the mRNA coding for the C-terminal portion of the endogenous βAPP protein in order not to interfere with the synthesis of the soluble functional recombinant form of the βAPP protein encoded by nucleic acids 201-2213 of SEQ ID NO:3.

9. The method of claim 8, wherein said soluble recombinant βAPP protein is overexpressed through a viral vector.

* * * * *

```
                          SEQUENCE LISTING

<160> NUMBER OF SEQ ID NOS: 3

<210> SEQ ID NO 1
<211> LENGTH: 21
<212> TYPE: RNA
<213> ORGANISM: artificial sequence
<220> FEATURE:
<223> OTHER INFORMATION: synthetic oligoribonucleotide

<400> SEQUENCE: 1
augaacuuca uauccugagu c                                             21

<210> SEQ ID NO 2
<211> LENGTH: 21
<212> TYPE: DNA
<213> ORGANISM: artificial sequence
<220> FEATURE:
<223> OTHER INFORMATION: synthetic oligonucleotide

<400> SEQUENCE: 2
gactcaggat atgaagttca t                                             21

<210> SEQ ID NO 3
<211> LENGTH: 3648
<212> TYPE: DNA
<213> ORGANISM: Homo Sapiens
<220> FEATURE:
<221> NAME/KEY: misc_feature
<223> OTHER INFORMATION: Encoding amyloid beta precursor protein (APP)

<400> SEQUENCE: 3
ggatcagctg actcgcctgg ctctgagccc cgccgccgcg ctcgggctcc gtcagtttcc      60
tcggcagcgg taggcgagag cacgcggagg agcgtgcgcg ggggccccgg gagacggcgg     120
cggtggcggc gcgggcagag caaggacgcg gcggatccca ctcgcacagc agcgcactcg     180
gtgccccgcg cagggtcgcg atgctgcccg gtttggcact gctcctgctg gccgcctgga     240
cggctcgggc gctggaggta cccactgatg gtaatgctgg cctgctggct gaaccccaga     300
ttgccatgtt ctgtggcaga ctgaacatgc acatgaatgt ccagaatggg aagtgggatt     360
```

```
cagatccatc agggaccaaa acctgcattg ataccaagga aggcatcctg cagtattgcc      420
aagaagtcta ccctgaactg cagatcacca atgtggtaga agccaaccaa ccagtgacca      480
tccagaactg gtgcaagcgg ggccgcaagc agtgcaagac ccatccccac tttgtgattc      540
cctaccgctg cttagttggt gagtttgtaa gtgatgccct tctcgttcct gacaagtgca      600
aattcttaca ccaggagagg atggatgttt gcgaaactca tcttcactgg cacaccgtcg      660
ccaaagagac atgcagtgag aagagtacca acttgcatga ctacggcatg ttgctgccct      720
gcggaattga caagttccga ggggtagagt ttgtgtgttg cccactggct gaagaaagtg      780
acaatgtgga ttctgctgat gcggaggagg atgactcgga tgtctggtgg ggcggagcag      840
acacagacta tgcagatggg agtgaagaca agtagtaga agtagcagag gaggaagaag      900
tggctgaggt ggaagaagaa gaagccgatg atgacgagga cgatgaggat ggtgatgagg      960
tagaggaaga ggctgaggaa ccctacgaag aagccacaga gagaaccacc agcattgcca     1020
ccaccaccac caccaccaca gagtctgtgg aagaggtggt tcgagaggtg tgctctgaac     1080
aagccgagac ggggccgtgc cgagcaatga tctcccgctg gtactttgat gtgactgaag     1140
ggaagtgtgc cccattcttt tacggcggat gtggcggcaa ccggaacaac tttgacacag     1200
aagagtactg catggccgtg tgtggcagcg ccatgtccca agtttactc aagactaccc      1260 aggaacctct tgcccgagat cctgttaaac ttcctacaac agcagccagt acccctgatg     1320
ccgttgacaa gtatctcgag acacctgggg atgaaatga acatgcccat ttccagaaag     1380
ccaaagagag gcttgaggcc aagcaccgag agaatgtc ccaggtcatg agagaatggg      1440
aagaggcaga acgtcaagca aagaacttgc ctaaagctga taagaaggca gttatccagc     1500
atttccagga gaaagtggaa tctttggaac aggaagcagc caacgagaga cagcagctgg     1560
tggagacaca catggccaga gtggaagcca tgctcaatga ccgccgccgc ctggccctgg     1620
agaactacat caccgctctg caggctgttc ctcctcggcc tcgtcacgtg ttcaatatgc     1680
taaagaagta tgtccgcgca gaacagaagg acagacagca caccctaaag catttcgagc     1740
atgtgcgcat ggtggatccc aagaaagccg ctcagatccg gtcccaggtt atgacacacc     1800
tccgtgtgat ttatgagcgc atgaatcagt ctctctccct gctctacaac gtgcctgcag     1860
tggccgagga gattcaggat gaagttgatg agctgcttca gaaagagcaa aactattcag     1920
atgacgtctt ggccaacatg attagtgaac caaggatcag ttacggaaac gatgctctca     1980
tgccatcttt gaccgaaacg aaaaccaccg tggagctcct tcccgtgaat ggagagttca     2040
gcctggacga tctccagccg tggcattctt ttggggctga ctctgtgcca gccaacacag     2100
aaaacgaagt tgagcctgtt gatgcccgcc ctgctgccga ccgaggactg accactcgac     2160
caggttctgg gttgacaaat atcaagacgg aggagatctc tgaagtgaag atggatgcag     2220
aattccgaca tgactcagga tatgaagttc atcatcaaaa attggtgttc tttgcagaag     2280
atgtgggttc aaacaaaggt gcaatcattg gactcatggt gggcggtgtt gtcatagcga     2340
cagtgatcgt catcaccttg gtgatgctga agaagaaaca gtacacatcc attcatcatg     2400
gtgtggtgga ggttgacgcc gctgtcaccc cagaggagcg ccacctgtcc aagatgcagc     2460
agaacggcta cgaaaatcca acctacaagt tctttgagca gatgcagaac tagaccccg      2520 ccacagcagc ctctgaagtt ggacagcaaa accattgctt cactacccat cggtgtccat     2580
ttatagaata atgtgggaag aaacaaaccc gtttttatgat ttactcatta tcgccttttg    2640
acagctgtgc tgtaacacaa gtagatgcct gaacttgaat taatccacac atcagtaatg    2700
tattctatct ctctttacat tttggtctct atactacatt attaatgggt tttgtgtact     2760
```

```
gtaaagaatt tagctgtatc aaactagtgc atgaatagat tctctcctga ttatttatca    2820
catagcccct tagccagttg tatattattc ttgtggtttg tgacccaatt aagtcctact    2880
ttacatatgc tttaagaatc gatgggggat gcttcatgtg aacgtgggag ttcagctgct    2940
tctcttgcct aagtattcct ttcctgatca ctatgcattt taaagttaaa cattttaag    3000 tatttcagat gctttagaga gatttttttt ccatgactgc attttactgt acagattgct    3060
gcttctgcta tatttgtgat ataggaatta agaggataca cacgtttgtt tcttcgtgcc    3120
tgttttatgt gcacacatta ggcattgaga cttcaagctt ttcttttttt gtccacgtat    3180
ctttgggtct ttgataaaga aaagaatccc tgttcattgt aagcactttt acggggcggg    3240
tggggagggg tgctctgctg gtcttcaatt accaagaatt ctccaaaaca attttctgca    3300
ggatgattgt acagaatcat tgcttatgac atgatcgctt tctacactgt attacataaa    3360
taaattaaat aaaataaccc cgggcaagac ttttctttga aggatgacta cagacattaa    3420
ataatcgaag taattttggg tggggagaag aggcagattc aattttcttt aaccagtctg    3480
aagtttcatt tatgatacaa aagaagatga aaatggaagt ggcaatataa ggggatgagg    3540
aaggcatgcc tggacaaacc cttcttttaa gatgtgtctt caatttgtat aaaatggtgt    3600
tttcatgtaa ataaatacat tcttggagga gcaaaaaaaa aaaaaaaa               3648
```